United States Patent [19]

D'Souza et al.

[11] 4,340,729
[45] Jul. 20, 1982

[54] 5'-DEOXY-5-FLUOROURIDINE

[75] Inventors: Richard D'Souza, Basel; Joseph Kiss, Arlesheim, both of Switzerland

[73] Assignee: Hoffmann-La Roche Inc., Nutley, N.J.

[21] Appl. No.: 156,590

[22] Filed: Jun. 5, 1980

[30] Foreign Application Priority Data

Jun. 12, 1979 [CH] Switzerland .................. 5625/79

[51] Int. Cl.$^3$ .............................. C07H 19/06
[52] U.S. Cl. .................................. 536/23; 536/4.1; 536/18.2
[58] Field of Search .............................. 536/23

[56] References Cited

U.S. PATENT DOCUMENTS 4,071,680  1/1978  Cook ................................ 536/23
4,122,251 10/1978  Misaki et al. ...................... 536/23

FOREIGN PATENT DOCUMENTS 1812268  6/1970  Fed. Rep. of Germany .
1489919  7/1966  France .

OTHER PUBLICATIONS

Chemical Abstract 77, 126977g (1972).
Angew, Chemie, Int. Ed. 14, 421 (1975).
J. Med. Chem., 11, 148–151 (1968).
J. Heterocycl. Chem. 9, 445–446 (1972).
Nucleic Acids Res. 3, 1125–37 (1976).

Primary Examiner—Blondel Hazel
Attorney, Agent, or Firm—Jon S. Saxe; George M. Gould; John B. Wilson

[57] ABSTRACT

A process for the manufacture of 5'-deoxy-5-fluorouridine which is a potent antitumor agent. The process comprises cleaving the acyl groups from a 1-(5-deoxy-2,3-di-O-acyl-β-D-ribofuranosyl)-5-fluorouracil, a novel intermediate in the process.

2 Claims, No Drawings

5'-DEOXY-5-FLUOROURIDINE

BACKGROUND OF THE INVENTION

5'-deoxy-5-fluorouridine is a known compound (e.g. from U.S. Pat. No. 4,071,680) having very good cytostatic activity. This compound is obtainable in a multistage synthesis from 5-fluorouridine, whereby the elimination of the 5'-hydroxy group is effected via the corresponding 5'-iodo compound.

DETAILED DESCRIPTION OF THE INVENTION

The present invention relates to a novel process for the manufacture of 5'-deoxy-5-fluorouridine and the acid addition salts thereof in very good yield and in a simple manner from a 5-deoxy-1,2,3-tri-O-acyl-D-ribofuranoside and 2,4-bis-O-(trimethylsily)5-fluorouracil followed by cleavage of the two acyl groups from the resulting novel intermediate 1-(5-deoxy-2,3-di-O-acyl-β-D-ribofuranosyl)-5-fluorouracil. The starting material for 5-deoxy-1,2,3-tri-O-acyl-D-ribofuranoside is readily obtainable from D-ribose or from methyl 2,3-O-isopropylidene-D-ribofuranoside.

The invention includes the novel intermediates produced by the invention process. Such novel intermediates include: methyl (5-deoxy-5-bromo-2,3-O-isopropylidene)-D-ribofuranoside and 1-(5-deoxy-2,3-di-O-acyl-β-D-ribofuranosyl)-5-fluorouracil and the acid-addition salts thereto. The following reaction scheme gives a synopsis of the preferred embodiment of the invention process as indicated by the reaction processes designated alphabetically from A to F in the scheme.

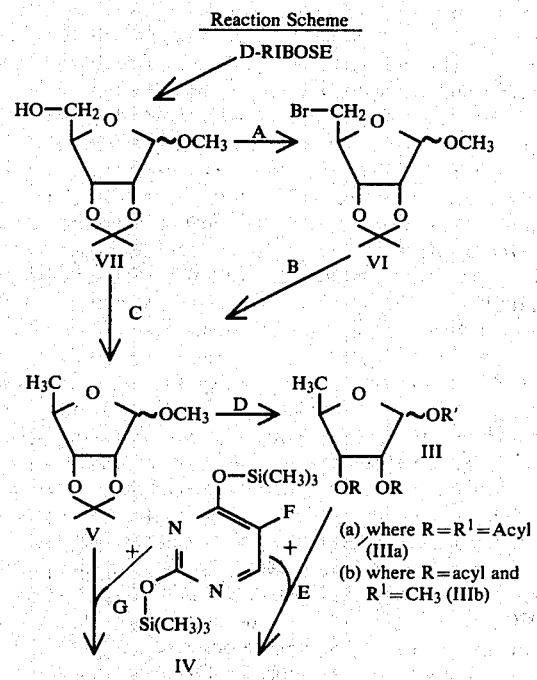

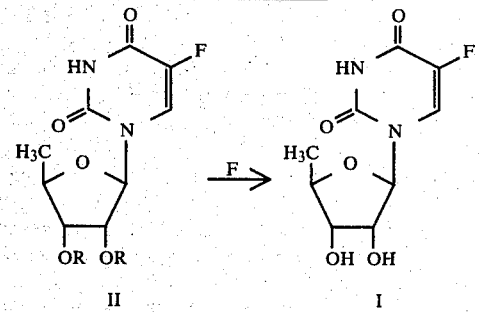

In accordance with the above reaction scheme the process of the present invention provides 5'-deoxy-5-fluorouridine or its acid addition salts, preferrably through reaction steps designated A to F. The starting material for reaction A is methyl 2,3-O-isopropylidene-D-ribofuranoside (formula VII) which is a known compound and which is readily obtainable from D-ribose by methods known per se in the art.

Reaction A of the scheme is a novel process and produces the novel intermediate methyl (5-deoxy-5-bromo-2,3-O-isopropylidene)-D-ribofuranoside (formula VI). Both the process and the intermediate form part of the present invention. In particularly the process of reaction A comprises replacement of the 5-hydroxy group of the compound of formula VII by a bromine atom using a novel bromination method. The novel bromination method reacts the compound of formula VII with bromine in a suitable organic solvent such as methylene chloride and in the presence of triphenylphosphine. The bromination reaction may be carried out in a temperature range from about 0° to about 60° C. Room temperature is preferred. The resulting reaction follows a simple course from which very pure product can be obtained in high yield, provided that the reaction is carried out anhydrously; that is, with the strict exclusion of water.

Reaction B of the scheme produces methyl (5-deoxy-2,3-O-isopropylidene)-D-ribofuranoside (formula V) from the compound of formula VI in a manner known per se whereby the bromine atom is reductively eliminated from the compound of formula VI. More particularly the novel compound of formula VI can readily be converted into the corresponding 5-deoxy compound of formula V by a catalytic hydrogenation reaction in a protic solvent as for example an alcohol, preferably such as methanol, in the presence of a noble metal catalyst, for example palladium, optionally supported on an inert carrier material such as carbon or barium sulphate, or also in the presence of Raney nickel. The hydrogenation reaction can be carried out at a temperature between 0° C. and 60° C. Room temperature is preferred. A pressure of 1 to 5 atmospheres is suitable, but normal pressure is preferred. The reaction is also preferably carried out in the presence of an inorganic or organic base such as potassium hydroxide or triethylamine.

On the other hand, the compound of formula V can also be obtained from the compound of formula VII by reaction C of the reaction scheme, comprising acylating, preferably acetylating, the latter in the 5-position and subsequently irradiating, preferably with a mercury high-pressure lamp, in hexamethylphosphoric acid triamide in the presence of a small amount of water (about 5%) and under a protective gas (e.g. argon) for several hours.

Reaction D of the scheme produces 5-deoxy-1,2,3-tri-O-acyl-D-ribofuranoside (formula IIIa) or a 5-deoxy-2,3-di-O-acyl-1-O-methyl-D-ribofuranoside (formula IIIb) from compounds of formula V. More particularly compounds of formula IIIa is obtained by hydrolysing the compound of formula V with an aqueous mineral acid in a manner known per se to provide 5-deoxy-D-ribose which is then acylated in a manner known per se to form the compound of formula IIIa. Preferably the 5-deoxy-D-ribose is acetylated using acetic anhydride in pyridine. The compound of formula IIIb can be obtained by selective cleavage of the isopropylidene group of compound of formula V as for example by treatment of compound of formula V for 10 minutes with a diluted acid such as 0.01 N hydrochloride, and then subsequent acylation using for example acetic anhydride in pyridine.

The acyl groups, as represented by the symbol R and $R^1$ where R represents acyl and $R^1$ represents $CH_3$ or acyl, may be selected from various residues of aliphatic or aromatic acids which are known in the art to which this invention relates as protecting groups in sugar chemistry. Of the known protecting groups the benzoyl and acetyl groups are preferred.

Compounds of the formula 1-(5-deoxy-2,3,di-O-acyl-β-D-ribofuranosyl)-5-fluorouracil (formula II) are prepared by reaction E of the scheme by reacting compounds of formula IIIa or IIIb in the form of the anomer mixture with 2,4-bis (trimethylsilyl)-5-fluorouracil (formula IV). This reaction is carried out in the presence of a suitable catalyst, preferably trimethylsilyl-trifluoromethanesulphonate or tin tetrachloride, at room temperature or lower, preferably while cooling with ice, in an inert organic solvent. Thereafter the desired β-anomer is isolated or separated from the reaction mixture. This separation proceeds especially simply and almost quantitatively in the case of the compound of formula I, since the β-anomer itself is very difficult to solubilize in hot ethyl acetate.

On the other hand a compound of formula II can also be prepared from the compound of formula V by reaction G. This can be accomplished by converting the compound of formula V in a manner known per se by selective cleavage of the isopropylidene group and subsequently acylating into a methyl (5-deoxy-2,2-di-O-acyl)-D-ribofuranoside. The resulting compound is then reacted with compound of formula IV in the manner described earlier. This route produces, however, a comparatively lower yield of compound of formula II.

Compounds of formula II as well as the process of reaction D represent novel compounds and a novel process and form part of the invention.

The final process of the reaction scheme is reaction F whereby the acyl groups of compounds of formula II are cleaved.

The cleavage of the acyl group from the compound of formula II is carried out in a manner known per se and proceeds almost quantitatively. The cleavage can be carried out by acid or alkaline hydrolysis; for example, in aqueous or alcoholic medium using an inorganic mineral acid such as hydrochloride, hydrobromide, phosphate, sulfate or the like or a strong organic acid such as p-toluenesulfonic acid. The hydrolysis is preferably carried out in an anhydrous alcoholic medium such as methanol by treatment with an alkali metal alcoholate such as sodium methylate. In this hydrolysis process an ester such as methyl acetate is produced as a by-product. For the cleavage to proceed quantitatively, the methyl acetate formed must be removed continuously or by repeated vacuum distillation. The cleavage of the acyl groups of formula II can also be carried out by treatment with a strong organic base (e.g. a trialkylamine such as triethylamine) in an organic solvent, preferably methanol, or by means of a strong basic ion exchanger (OH form).

The working-up of the reaction mixture can be carried out in the usual manner. The neutralization of the mixture is advantageously carried out by treatment with a cation exchanger ($H^+$form). The 5'-deoxy-5-fluorouradine in solution can be obtained in a high yield and purity from the solution by concentration after removal of the exchange resin.

The final product, 5'-deoxy-5-fluorouridine, and its pharmaceutically acceptable acid-addition salts are useful as anti-tumor agents. The salts of the final product include non-toxic salts such as formed from acids selected from the group consisting of inorganic mineral acids such as hydrochloride, hydrobromide, phosphate, sulphate or nitrate, or from organic acids such as acetate, formate, meleate, benzoate and the like.

The following examples further illustrate the invention but are not means to limit the invention in scope or spirit.

EXAMPLE 1

A. Preparation of the starting material

A solution of 204.22 g of methyl 2,3-O-isopropylidene-D-ribofuranoside and 524.5 g of triphenylphosphine in 7000 ml of methylene chloride was cooled to 5°–8° C. and treated within 60 minutes while stirring with 102 ml of bromine. The mixture was heated under reflux for 4 hours and subsequently stirred at room temperature for 14 hours. After the addition of 50 ml of methanol, the mixture was washed four times each with 2000 ml of water, with 2000 ml of 3% aqueous sodium hydrogen carbonate solution and again with 2000 ml of water. The organic phase was dried over anhydrous sodium sulphate and concentrated to about 1000 ml under reduced pressure and while warming slightly. The concentrated solution was treated with 1000 ml of hexane and the crystals formed were filtered off under suction and washed twice with 300 ml of hexane each time. The residue obtained from the combined solutions by evaporation was extracted twice with 1000 ml of hexane each time and finally eluted on a silica gel column (6×80 cm) using 1500 ml of hexane. The combined hexane solutions yielded, after concentration in vacuo and subsequent vacuum distillation, 226 g (85%) of methyl (5-deoxy-5-bromo-2,3-O-isopropylidene)-D-ribofuranoside; b.p.$_{.06}$=72° C.; $n_D^{24}$=1.4712; $(\alpha)_D^{364}$=237.6° (1% in chloroform).

802 g of methyl (5-deoxy-5-bromo-2,3-O-isopropylidene)-D-ribofuranoside in 7500 ml of methanol were hydrogenated at room temperature in the presence of methanolic potassium hydroxide (185 g in 3000 ml of methanol) and 50 g of 5% palladium/carbon for 15 hours. The mixture was filtered, the filtrate was concentrated at 35° C. under reduced pressure and the residue was diluted with 2000 ml of hexane and added to a silica gel column (5×80 cm) which was eluted with 4000 ml of hexane. After evaporation of the eluate and vacuum distillation, there were obtained 510 g of (90%) of methyl (5-deoxy-2,3-O-isopropylidene)-D- ribofuranoside; b.p$_{10-12}$ 72°–75° C.; n$_D^{20}$=1.4340; [α]$_D^{25}$=−96.6° (c=0.34 in chloroform).

A mixture of 282 g of methyl (5-deoxy-2,3-O-isopropylidene)-D-ribofuranoside, 162 ml of 1 N hydrochloric acid and 3860 ml of water was heated at 110° C. for 2 hours while stirring. The solution was cooled to 16°–20° C. by pouring in ice/water and neutralised by the addition of 1000 ml of a strongly basic anion exchanger (OH$^-$— form). After stirring for 30 minutes, the pH value of the mixture was 6. The ion exchanger was filtered off and washed with 2000 ml of water. The aqueous solutions were concentrated 25 40°–45° C. under reduced pressure and the oily residue was evaporated in the presence of 3000 ml of pyridine. The crude 5-deoxy-D-ribose obtained (202 g) was dissolved in 3000 ml of pyridine and acetylated by treatment with 720 g of acetic anhydride. The mixture was left to stand at room temperature for 20 hours, concentrated under reduced pressure to a volume of 400–500 ml and, while stirring, poured into 2000 ml of a saturated aqueous sodium hydrogen carbonate solution. The aqueous solution was extracted twice with 1000 ml of methylene chloride each time, the extract was washed twice with 1000 ml of water each time, dried over anhydrous sodium sulphate and concentrated under reduced pressure. The syrupy residue was evaporated twice after the addition of, in each case, 2000 ml of toluene, taken up in 1000 ml of ether, the ethereal phase was evaporated and purified by vacuum distillation (b.p.$_{0.1-0.3}$=96°–102° C.). There were obtained 210 g (75%) of 5-deoxy-1,2,3-tri-O-acetyl-D-ribofuranoside as the anomer mixture. The crystalline β-anomer isolated therefrom has a melting point of 66°–67° C.

A solution of 305 g of freshly distilled 5-deoxy-1,2,3-tri-O-acetyl-D-ribofuranoside (anomer mixture) in 300 ml of methylene chloride was treated with 2,4-bis(-trimethylsilyl)-5-fluorouracil, freshly prepared from 165 g of 5-fluorouracil and 620 ml of hexamethyldisilazane, in 1000 ml of methylene chloride. The reaction was carried out while cooling with ice and stirring vigorously in the presence of 230 ml of trimethylsilyl-trifluoro-methane-sulphonate in 250 ml of methylene chloride. The mixture was left to stand at room temperature for 20 hours, poured into 3000 ml of saturated aqueous sodium hydrogen carbonate solution, stirred for 30 minutes and extracted three times with 800 ml of methylene chloride each time. The extracts were washed three times with 300 ml of water each time, dried over anhydrous sodium sulphate and concentrated under reduced pressure to a volume of 500–600 ml. The concentrate was treated with 500 ml of hexane and the solution was evaporated at room temperature within about 2 hours. The crystalline produce obtained was washed with a mixture, cooled to 0° C., of 900 ml of ethyl acetate and 900 ml of hexane and heated under reflux for 10 minutes with 500 ml of ethyl acetate. The solution was cooled and left to stand to 12 hours in a refrigerator. There were obtained 250 g of pure 1-(5-deoxy-2,3-di-O-acetyl-β-D-ribofuranosyl)-5-fluorouracil, m.p. 176°–177° C.

B. Manufacture of 5-deoxy-5-fluorouridine from 1-(5-deoxy-2,3-di-O-acetyl-β-D-ribofuranosyl)-5-fluorouracil A solution of 860 g of 1-(5-deoxy-2,3-di-O-acetyl-β-D-ribofuranosyl)-5-fluorouracil in 16 liters of methanol was added to sodium methoxide freshly prepared from 42 g of sodium and 2000 ml of methanol. The methyl acetate resulting during the reaction was removed by repeated concentration of the mixture. The mixture was neutralised by the addition of 1000 ml of a strongly acidic cation exchange resin (H$^+$-form), freshly washed with methanol. After removing the ion exchange resin, the methanolic solution was concentrated under reduced pressure and the product, which separated in crystalline form, was washed with a mixture, cooled to 0° C., of 1000 ml of methanol and 1000 ml of ethyl acetate. By working-up the mother liquors there was obtained a total of 680 g (97%) of pure 5'-deoxy-5-fluorouridine; m.p. 192°–193° C.; [β]$_D^{25}$=+139° (c=0.9 in methanol).

EXAMPLE 2

A solution of 100 g of methyl (5-deoxy-2,3-O-isopropylidene)-D-ribofuranoside in 500 ml of methanol was treated with 500 ml of 0.1 N sulphuric acid and the mixture was heated under reflux on a water-bath until starting material could no longer be detected by thin-layer chromatography. The mixture was then neutralized (pH 6–7) by the addition of barium carbonate while stirring, filtered under suction over a glass frit and the filtrate was concentrated to dryness under reduced pressure. The residue was taken-up twice in a mixture of 150 ml of methanol and 100 ml of benzene, again concentrated and finally taken-up in 500 ml of dry pyridine and 400 ml of acetic anhydride. After standing at 20°–22° C. for 24 hours the mixture was concentrated under reduced pressure, taken-up twice with 200 ml of toluene each time and then concentrated. The residue was dissolved in 300 ml of methylene chloride. The solution was washed twice with 150 ml of 1 N sulphuric acid each time and with 100 ml of 2% sodium hydrogen carbonate solution, dried over sodium sulphate and concentrated under reduced pressure. There were obtained 130 g of crude methyl(5-deoxy-2,3-di-O-acetyl)-D-ribofuranoside in the form of a yellowish, oily material which was distilled under reduced pressure; b.p.$_{0.3}$78°–79° C.; n$_D^{20}$=1.4371–1.4380.

30 ml of a solution of 2,4-bis (trimethylsilyl)-5-fluorouracil (prepared from 5.2 g of fluorouracil and 20 ml of hexamethyldisilazane) in methylene chloride were added to a solution of 8.1 g of freshly distilled methyl (5-deoxy-2,3-di-O-acetyl)-D-ribofuranoside in 81 ml of methylene chloride. The mixture was cooled in ice and treated while stirring with a solution of 7 ml of trimethylsilyl-trifluoro-methanesulphonate in 8 ml of methylene chloride. The mixture was left to stand at room temperature for 20 hours, poured into 200 ml of saturated aqueous sodium hydrogen carbonate solution, the mixture was stirred for 30 minutes and then extracted 3 times with 100 ml of methylene chloride each time. The combined extracts were washed twice with 50 ml of water each time, dried over anhydrous sodium sulphate, concentrated to 60 ml under reduced pressure without heating and, after the addition of 60 ml of hexane, concentrated under the same conditions. The residue was left to stand for 4 hours in a refrigerator, the crystals were filtered off, washed with a cold 1:1 mixture of ethyl acetate and hexane and finally with ethyl acetate. There were obtained 7 g of pure 1-(5-deoxy-2,3-di-O-acetyl-β-D-ribofuranosyl)-5-fluorouracil, m.p. 179°–181° C.; [β]$_D^{20}$=+34.6° (c=1.0 in methanol).

2.5 g of 1-(5-deoxy-2,3-di-O-acetyl-β-D-ribofuranosyl)-5-fluorouracil were heated under reflux in 60 ml of methanol in the presence of 0.3 ml of triethylamine until starting material could no longer be detected by thin-layer chromatography. The colourless, clear solution was concentrated under reduced pressure and the white, crystalline material obtained was recrystallised from water. There was obtained pure 5'-deoxy-5-fluorouridine, m.p. 192°–193° C., in 98% yield.

We claim:

1. A compound of the formula 1-(5-deoxy-2,3-di-O-acyl-β-D-ribofuranosyl)-5-fluorouracil wherein acyl represents a group which is a residue of an aliphatic or aromatic acid capable of being used as a protecting group in sugar chemistry.

2. A compound according to claim 1 which is 1-(5-deoxy-2,3-di-O-acetyl-β-D-ribofuranosyl)-5-fluorouracil.

* * * * *